(12) United States Patent
Mehier

(10) Patent No.: US 8,337,491 B2
(45) Date of Patent: Dec. 25, 2012

(54) INSTALLATION FOR DELIVERING HEAT TO ALL OR PART OF HUMAN OR ANIMAL CELL TISSUE

(75) Inventor: Henri Mehier, Lyons (FR)

(73) Assignee: Centre d'Etude et de Recherche Medicale d'Archamps—CERMA, Archamps (FR)

(*) Notice: Subject to any disclaimer, the term of this patent is extended or adjusted under 35 U.S.C. 154(b) by 1396 days.

(21) Appl. No.: 11/966,716

(22) Filed: Dec. 28, 2007

(65) Prior Publication Data

US 2008/0103566 A1 May 1, 2008

Related U.S. Application Data

(63) Continuation of application No. 10/894,183, filed on Jul. 19, 2004, now Pat. No. 7,335,195, which is a continuation of application No. PCT/FR03/00192, filed on Jan. 21, 2003.

(30) Foreign Application Priority Data

Feb. 21, 2002 (FR) .................................. 02 02213

(51) Int. Cl.
*A61B 18/04* (2006.01)

(52) U.S. Cl. .......................................... 606/27; 607/105
(58) Field of Classification Search .............. 606/27–31, 606/41, 48–50; 607/101–105; 604/113, 604/114
See application file for complete search history.

(56) References Cited

U.S. PATENT DOCUMENTS

| | | | | |
|---|---|---|---|---|
| 5,073,167 A | * | 12/1991 | Carr et al. ...................... | 604/114 |
| 5,180,896 A | * | 1/1993 | Gibby et al. ................... | 219/687 |
| 5,505,729 A | * | 4/1996 | Rau ................................. | 606/40 |
| 6,024,095 A | * | 2/2000 | Stanley, III .................... | 128/898 |
| 6,508,816 B2 | * | 1/2003 | Shadduck ....................... | 606/34 |

* cited by examiner

*Primary Examiner* — Michael Peffley
(74) *Attorney, Agent, or Firm* — Heslin Rothenberg Farley & Mesiti P.C.; Victor A. Cardona

(57) ABSTRACT

An installation for delivering calories to all or part of human or animal cell tissue via a liquid comprises: a heating unit heating the liquid; an injection unit injecting the liquid into the heating unit; a dispenser for dispensing the heated liquid; and a transporter for transporting the liquid from the heating unit to the dispenser. The installation allows the heated liquid to be dispensed from the dispensing means in a pulsed operation.

8 Claims, 2 Drawing Sheets

Figure 1:
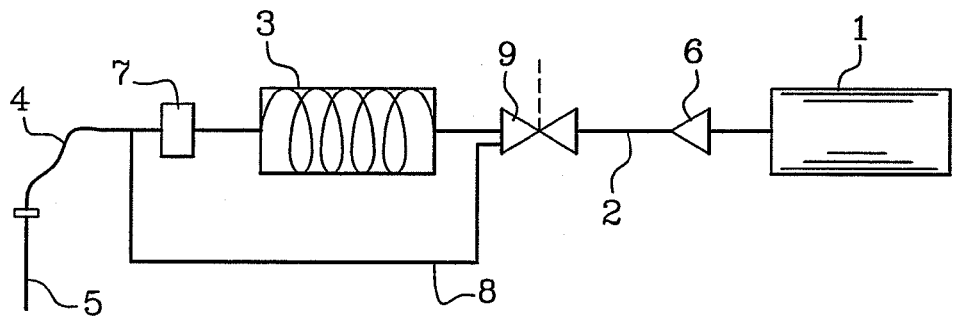

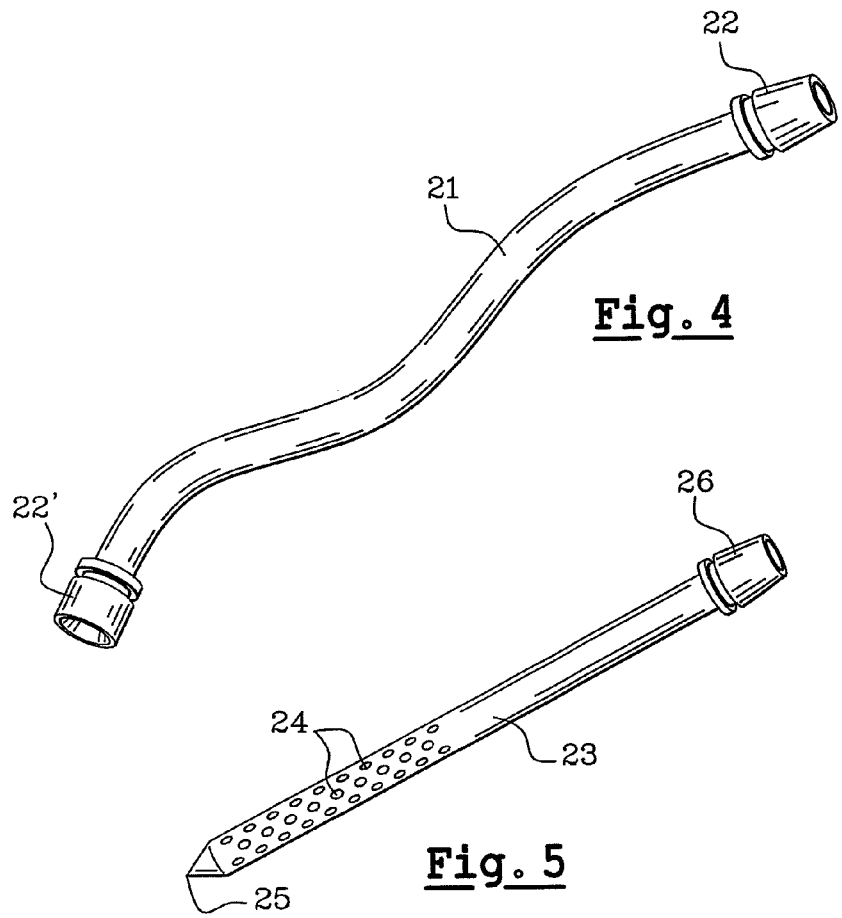
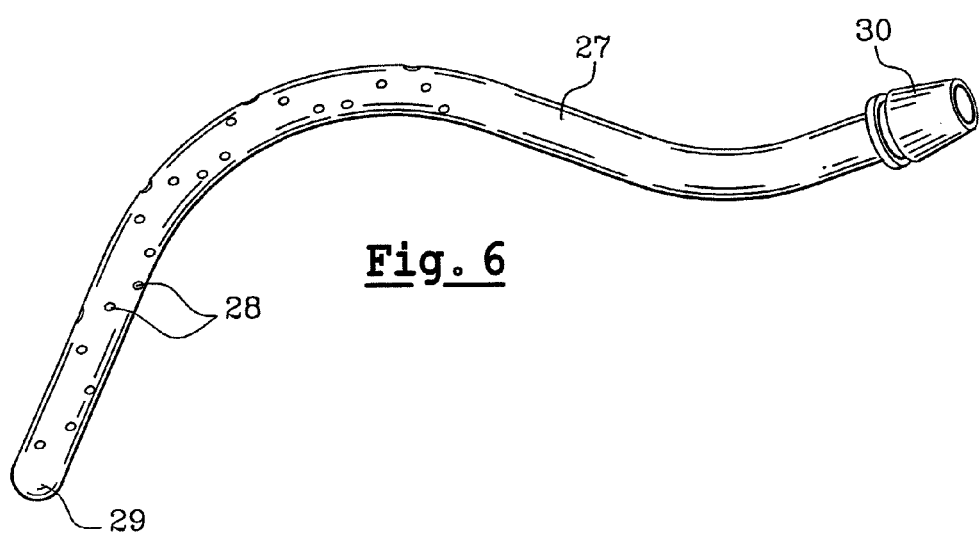

INSTALLATION FOR DELIVERING HEAT TO ALL OR PART OF HUMAN OR ANIMAL CELL TISSUE

CROSS REFERENCE TO RELATED APPLICATIONS

This application is a continuation of U.S. patent application Ser. No. 10/894,183, filed Jul. 19, 2004, now U.S. Pat. No. 7,335,195, which is a continuation of international application PCT/FR03/00192 filed Jan. 21, 2003 and published, in French, as international publication number WO 03/070302 A1 on Aug. 28, 2003, which claims priority from French patent application number 02.02213 filed Feb. 21, 2002, the entire disclosures of which are incorporated herein by reference.

The invention concerns an installation for delivering heat to all or part of human or animal cell tissue by means of a liquid. More precisely, it relates to an apparatus with which it is possible to inject a heat transfer liquid, chosen from the group comprising water, oxygenated water and ethanol, into all or part of organs, in particular into the area of cancer cells.

One of the methods of treating cancerous tumors involves destroying all or part of the cancerous tissue by targeted administration of heat or cold. This principle is known by the name thermal ablation and is presently used in particular in the treatment of liver metastases.

Several techniques based on the principle of thermal ablation by heat are available nowadays, for example laser thermal ablation, radiofrequency thermal ablation with needle, and cryotherapy, which for its part involves thermal ablation by cold. However, these techniques have a number of disadvantages. In particular, the volume of the tumor treated is limited (in practice from 4 to 5 cm in diameter) and the intervention time is relatively long, from 20 to 30 minutes for radiofrequency thermal ablation and cryotherapy, and even more for laser treatment.

The document WO 00/29055 from the Applicant describes a thermal ablation technique by heat which consists in injecting a physically active substance, in practice water or oxygenated water in pressurized form, into a flexible hollow tube provided with apertures and "sewn" inside the organ to be treated. The temperature of the pressurized liquid, in contact with the tissue to be treated, decreases and the water or oxygenated water becomes liquid again within the tumor. The pressurized liquid is obtained and injected by means of an apparatus composed of a heating unit in the form of a metal coil on which a stainless steel tube is wound, directly connected to the microperforated tube. The water travels through and is heated in the stainless steel tube, in the area of this unit, to a temperature of about 400° C. and a pressure of about 250 bar.

In the course of his research, the Applicant has discovered that the delivery of water or oxygenated water to a tumor ought advantageously to be done using small volumes of water which are injected in pulsed form, both for reasons of effectiveness and for reasons of safety.

The use of small volumes of water, in practice of between 0.2 and 1 ml, in fact avoids the risks of heat diffusion outside the tumor and, consequently, the destruction of healthy tissues. The Applicant has in addition found that administration of small volumes of water or oxygenated water at regular intervals, in practice of between 0.5 and 1 second, allowed treatment of zones of greater volume and in a shorter time than with the known techniques of the prior art. In addition, the pulsed operation makes it possible to avoid heating of the part of the tube not in contact with the tumor, that is to say the part of the tube connecting the outside of the body, thus avoiding the destruction, by heat, of healthy tissues.

As has already been stated, the liquid intended to be injected is a physically active substance, in practice water, oxygenated water, or ethanol, the latter two having the advantage, in addition to the provision of heat, of being chemically aggressive with respect to the tumor to be treated.

The invention thus concerns an installation for delivering heat to all or part of human or animal cell tissue by means of a liquid, said installation comprising:

a heating unit for heating said liquid,
an injection unit for injecting liquid into the heating unit,
a means for diffusion of heated liquid,
a means for conveying the heated liquid from the heating unit to the diffusion means.

The installation is characterized in that it has means for delivering the heated liquid at the diffusion means in a pulsed mode.

In practice, the installation has means for pulsed delivery of the heated liquid at a pressure at least equal to the saturation vapor pressure of the liquid to be injected.

In the rest of the description, the installation will be illustrated using water as the liquid to be injected, although oxygenated water or ethanol can also be used.

According to a first characteristic of the invention, the injection unit is in the form of a chamber which contains the liquid to be injected and in which a piston is moved in translation under the action of an electric or pneumatic actuator whose triggering, travel, force and speed of displacement are determined as a function of the desired rhythm, volume and pressure of injection of the liquid, the chamber communicating with the heating unit by way of a first valve.

In other words, the injection unit constitutes the first element contributing to delivering heat in pulsed mode, by injecting a specified quantity of cold water at regular intervals into the heating unit, by virtue of the combination of the action of an actuator, whose triggering, travel, force and speed are programmed as a function of the desired rhythm, volume and pressure of injection, together with a valve which prohibits return of the liquid injected into the chamber.

More precisely, the triggering and the travel of the actuator are programmed as a function of the number of injections desired for delivering a defined volume of water, the latter depending directly on the size of the tumor to be treated. The Applicant has thus found that satisfactory tissue necrosis was obtained using a volume of pressurized water at 400° C. representing about 5% of the volume of the tumor to be treated. The triggering and the travel of the actuator are then programmed to obtain injected volumes of liquid of between 0.2 and 1 ml at regular intervals of 0.5 to 1 second. In practice, the travel of the actuator is programmed by regulating the number of revolutions of the motor operating the actuator.

Moreover, the pressure at which the liquid is injected depends on the speed of displacement and the force of the actuator, which are also programmed. In practice, the speed of displacement of the actuator is programmed by regulating the speed of rotation of the motor operating the actuator.

To be able to inject small volumes of water, it is necessary to heat the liquid to a very high temperature, for water or oxygenated water, for example, of the order of 400° C. and more. At such a temperature and at atmospheric pressure, the water or oxygenated water would be vaporized in the heating unit, thus prohibiting effective delivery, in pulsed form, of heat to the diffusion system. Consequently, to solve the double problem of keeping the substance in liquid form at such a temperature and of administering it in pulsed form with pulse durations of in practice between 0.1 and 0.2 second, the force and the speed are chosen in such a way that the liquid is injected into the heating unit at a pressure greater by at least 50 bar, advantageously 100 bar, than the saturation vapor pressure of said liquid to be injected. In the case of injection of water, the pressure of injection will be fixed at about 350 bar.

As has already been stated, the actuator is an electric or pneumatic actuator. When the treatment is carried out in proximity to magnetic resonance imaging equipment, the actuator must be nonmagnetic. In this case, it is advantageous to use a pneumatic actuator which drives small volumes of water into the heating unit until the desired volume is obtained.

According to another characteristic, the installation comprises a liquid storage reservoir intended to supply the chamber of the injection unit, said storage reservoir being fixed or removable. The supply of liquid to the chamber is advantageously carried out with predetermined volumes corresponding to the volume to be injected into the tumor. In all cases, the reservoir is separated from the chamber by a second valve prohibiting the return of the liquid into the chamber, under the action of the piston.

Once the cold liquid (for example water) under pressure is transmitted to the heating unit, the latter is heated to a temperature of 400° C. and more.

In an advantageous embodiment, and again for pulsed operation, the heating unit is in the form of a metal coil incorporating an electrical resistor or a heat exchanger around which there is wound a stainless steel tube, through which the liquid flows. The internal diameter of the tube is chosen so as to prohibit mixing of the hot water with the cold water at the time of the pulse. Moreover, the length of the tube is chosen in combination with the internal diameter depending on the volume to be injected.

In practice, the internal diameter is between 0.1 and 0.5 mm, advantageously 0.3 mm, the length of the tube varying as a function of the dimensions of the coil and being in practice between 1500 and 5000 mm. Likewise, the dimension of the external diameter of the stainless steel tube is between 1 and 2 mm, advantageously of the order of 1.5 mm.

When the treatment is carried out near magnetic resonance imaging equipment, the electrical resistor is replaced by a source supplied by a heat transfer fluid, the heat transfer fluid being heated remote from the heating unit and being carried through a nonmagnetic insulated tubing (between 1 and 2 meters).

According to another characteristic, in order to solve the problem of maintaining the liquid to be injected in pressurized form at the desired temperature as far as the diffusion means, the heating unit is separated from the conveying means either by a valve calibrated to a pressure at least equal to the saturation vapor pressure of the liquid to be injected, or by a valve capable of withstanding a high temperature and a high pressure, of the order of 400° C. and at least 350 bar, respectively; in practice of the order of 1000 bar. When the liquid to be injected is water, the valve is calibrated to 250 bar for 400° C.

In an advantageous embodiment, the installation comprises a cold water branch circuit whose point of departure is positioned between the injection unit and the heating unit, while the point of arrival is positioned downstream of the valve, said branch circuit being connected to the point of departure by means of a programmable high-pressure solenoid valve.

This cold water circuit has a double advantage. First, it makes it possible, during operation of the installation, to purge the hot water remaining in the diffusion means, thereby reducing heating outside the phases of injection, while at the same time accelerating the rhythm of the pulses. In addition, it constitutes a safety system in the event of too great a volume of hot water being injected, the operator then being able to inject cold water into the tumor.

In practice, the cold water circuit is in the form of a stainless steel tube whose external diameter is between 1.2 and 1.8 mm, while the internal diameter is between 0.1 and 0.5 mm.

According to another characteristic, the heating unit is separated from the diffusion means by a conveying means. To reduce the dead space present at the outlet of the heating unit to a maximum and to ensure delivery of pressurized liquid in pulsed form, the means for conveying the heated liquid is in the form of a hollow flexible tube which is able to withstand a high pressure and temperature and whose length is between 40 and 80 cm, while the external diameter is between 100 and 250 µm, and the internal diameter is between 50 and 150 µm. For water, the pressure and temperature are above 250 bar and 400° C., respectively. In practice, the tube is made of stainless steel of quality A305, titanium, or platinum/iridium alloy or nickel/titanium alloy. It can additionally be covered with a plastic sheath which withstands temperature and can be fairly rigid, for example of the silicone, polyamide or polyurethane type. The tube additionally has, at one of its ends, a first conical joint providing the junction with the heating unit, and a second conical joint for the junction with the diffusion means.

In other words, and as will be evident from the above, the combination of the characteristics:
- of the actuator, allowing cold water to arrive in pulsed form at the heating unit,
- of the stainless steel tube in which the liquid is heated, permitting propulsion of hot water at homogeneous and maximum temperature,
- of the valve, making it possible to maintain the pressure equal to the saturation vapor pressure of the liquid to be injected,
- of the conveying means, making it possible to reduce the dead volume to a maximum, ensures that water is delivered in pressurized form and in pulsed mode at the diffusion system.

The diffusion means can be of two types.

In a first embodiment, the diffusion means is in the form of a tube similar to the one described in the document WO 00/29055. More precisely, the diffusion means is in the form of a hollow tube whose walls are provided in whole or in part with apertures, in particular the walls in contact with the tissue to be treated, and whose distal end is closed. In practice, such a tube is intended to be made integral with the organ to be treated. As with the conveying means, it is made of a material of the titanium type, stainless steel, platinum/iridium alloy or nickel/titanium alloy, and more generally of any material capable of withstanding a pressure and a temperature greater than 250 bar and 400° C. respectively (in the case of water).

Furthermore, and according to another characteristic, the external diameter of the tube is between 100 and 250 µm, while the internal diameter is between 50 and 150 µm.

As has already been stated, it is provided with substantially circular apertures with a diameter of between 30 and 70 µm, advantageously 50 µm.

In a second embodiment, the conveying means is in the form of a rigid needle whose distal end is closed off and whose walls have, along all or part of the length of the needle, in particular the walls in contact with the tissue to be treated, apertures with a diameter of between 30 and 70 µm, advantageously 50 µm. According to a first characteristic, the internal diameter of the needle is between 0.05 and 0.2 mm, while the external diameter is between 0.2 mm and 0.7 mm, the length being between 100 and 200 mm. This needle is made of a material of the steel or stainless steel type, titanium or a metal alloy. The junction between the upstream end of the needle and the conveying means is advantageously provided by a weld or a conical joint.

The invention also concerns a method of treating all or part of a human or animal tissue by thermal ablation, in which method heat is delivered to said tissue by means of a liquid, in a pulsed mode.

In an advantageous embodiment, heat is delivered by means of a volume of liquid of between 0.2 and 1, at regular intervals of between 0.5 and 1 second, at a pressure at least equal to the saturation vapor pressure of the liquid to be injected.

In practice, the duration of the pulses is between 0.1 and 0.2 second.

The invention also concerns a method of administering heat by means of a liquid to all or part of a human or animal tissue with the aid of the apparatus described above, consisting in:
- positioning the diffusion means at the level of the organ to be treated,
- connecting said diffusion means to the conveying means, then connecting the conveying means to the assembly formed by the heating unit and the injection unit,
- programming the triggering, travel, speed and force of the actuator, as a function of the desired rhythm, volume and pressure of injection of the liquid,
- supplying the chamber of the injection unit with the desired volume of liquid to be injected,
- triggering the actuator,
- withdrawing the diffusion means once the desired volume of water has been injected at the desired temperature.

In an advantageous embodiment, the duration of the last pulse is prolonged for a same volume of water so as to heat the diffusion means and thus avoid dissemination of the cancerous cells outside the tumor at the time of withdrawal.

The invention and the advantages which it affords will become clearer from the following embodiment, with reference to the attached figures.

Figure 2:
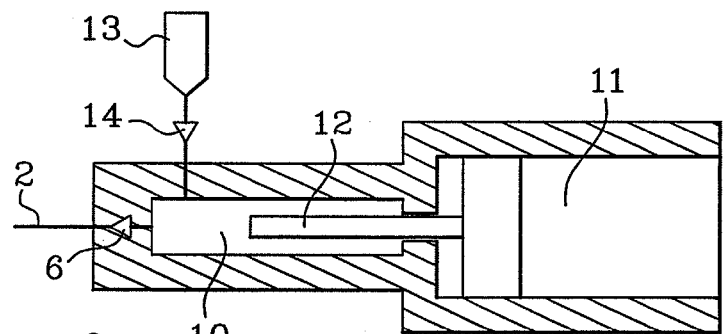
Figure 3:
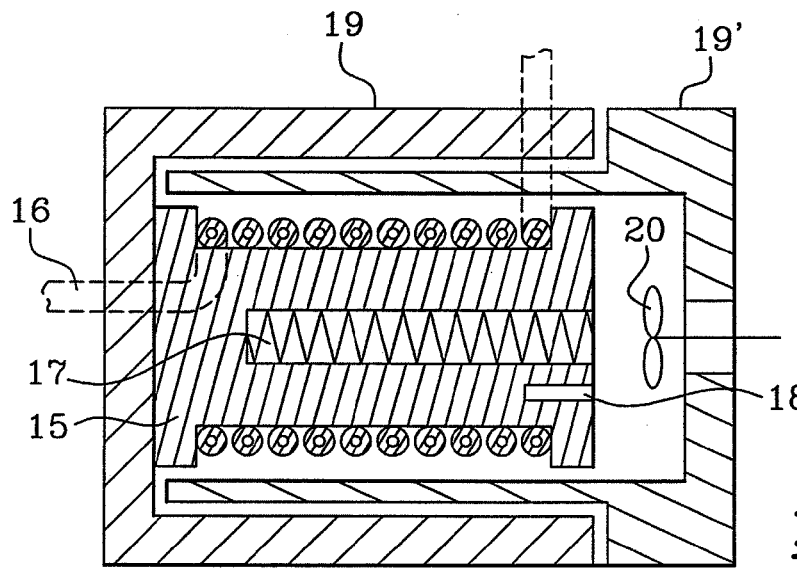

FIG. 1 is a diagrammatic representation of the installation.
FIG. 2 is a diagrammatic representation of the injection unit.
FIG. 3 is a diagrammatic representation of the heating unit.
FIG. 4 is a diagrammatic representation of the conveying means.
FIG. 5 is a diagrammatic representation of the diffusion means in the form of a needle.
FIG. 6 is a diagrammatic representation of the diffusion means in the form of a tube.

As is shown in FIG. 1, the installation according to the invention comprises 4 main elements, namely an injection unit (1) communicating, by way of a stainless steel tube (2), with a heating unit (3), a means of conveying hot liquid or extension piece (4), and a diffusion means (5). The external diameter of the stainless steel tube (2) is equal to 1.6 mm, while its internal diameter is equal to 0.25 mm.

According to a first characteristic of the invention, the injection unit is separated from the heating unit by a valve (6), the heating unit (3) being itself separated from the extension piece (4) by a valve (7).

In the advantageous embodiment, as shown in FIG. 1, the installation is completed by a cold water branch circuit (8) whose inlet is positioned between the injection unit (1) and the heating unit (3), while the outlet is positioned downstream of the valve (7). Moreover, the cold water circuit (8) communicates with the main hot water circuit at the entry point by way of a programmable solenoid valve (9).

Each element of the installation will now be discussed in detail.

First, as regards the injection unit (1), this is in the form of a cylinder provided with a chamber (10) in which a piston (12) is moved in translation under the action of an actuator (11). The actuator (11) can be an electric actuator or a pneumatic actuator depending on the environment in which it is used (nonmagnetic actuator needed or not). In the present embodiment, the actuator is an electric actuator whose triggering, travel (regulated by the number of revolutions of the motor), force (regulated by the power of the motor) and speed (regulated by the speed of rotation of the motor) are programmable. In this example, the force of the chosen actuator is equal to 10 kilonewtons for a surface of the piston less than 3 $cm^2$. When the liquid used is water, the actuator is able to inject cold water into the heating unit at a pressure of 350 bar.

The chamber (10) is additionally connected to a liquid storage reservoir (13) which supplies liquid to the chamber. The liquid reservoir (13) is additionally separated from the chamber (10) by way of a second valve (14).

The heating unit (3) represented diagrammatically in FIG. 3 is in the form of an aluminum coil (15) with a diameter equal to 50 mm and a length equal to 100 mm, around which is wound a stainless steel tube (16) with an external diameter equal to 1.6 mm and an internal diameter equal to 0.25 mm, and a length of between 1500 and 5000 mm, constituting the prolongation of the tube (2). The assembly of coil (15)/stainless steel tube (16) incorporates an electrical resistor (17). The coil (15) is additionally provided with a probe (18) regulating the temperature of the coil. The coil is also held in two concentric tubes (19, 19') permitting thermal insulation and cooling of the system in combination with a ventilator (20).

The extension piece (4) as shown in FIG. 4 is for its part in the form of a hollow tube (21) with a length equal to 50 cm and internal and external diameters equal to 100 μm and 200 μm, respectively. This tube is made of stainless steel of A305 quality and covered with a plastic sheath of the silicone type. The conveying means also has, at its upstream end, a first conical joint (22) permitting connection to the heating unit, and a second conical joint (22') permitting connection to the diffusion means.

As has already been stated, the conveying means (4) is separated from the heating unit (3) by way of a valve (7). According to an important characteristic, the valve is calibrated to a pressure at least equal to the saturation vapor pressure of the liquid to be injected. When the liquid injected is water, the valve (7) is calibrated to 250 bar (400° C.).

Two types of diffusion means can be used.

The first type, shown in FIG. 5, corresponds to a steel needle (23) with a length equal to about 20 cm, closed at its distal end (25) and provided with apertures (24) along all or part of its height, in particular in the zone intended to be in contact with the tissue to be treated. The external diameter of the needle is 0.5 mm, while the internal diameter is equal to 0.2 mm. In addition, the apertures have a diameter equal to 50 μm. In practice, the extension piece (21) is connected to the needle by a weld (26).

In a second embodiment shown in FIG. 6, the diffusion means (5) is in the form of a tube (27) intended to be sewn directly in the area of the tissue. The tube (27) is provided with apertures (28) of a size equal to 70 μm in diameter and formed on all or part of the length of the tube, in particular in the part intended to be in contact with the tissue. The tube is additionally closed at its distal end (29). The external diameter of the tube is equal to 200 µm, while the internal diameter is equal to 100 µm. In the same way as for the needle, the upstream end of the tube is provided with a conical joint (30).

The installation is used in the following way.

In a first stage, a needle (23) or tube (27) is chosen having a distribution of the apertures adapted to the size of the tumor to be treated. When the diffusion means (5) is in the form of a tube, the latter is positioned in the tissue to be treated, advantageously by way of a biopsy needle of greater diameter serving as a guide. Once in position, the free end of the tube (27) communicates with the outside of the body. The diffusion means is then connected to the extension piece (3) by way of the conical joint (30). The free end of the extension piece (hollow tube) (21) is then connected to the assembly of heating unit (3)/injection unit (1) by way of the conical joint (22). When the diffusion means is in the form of a needle, the welded assembly of needle/extension piece (26) is positioned in the area of the tumor to be treated.

The operator then determines the volume of water to be injected as a function of the size of the tumor. Based on his experience, the Applicant has found that it was generally necessary to inject a volume of liquid representing 5% of the volume of the tumor to be treated in order to obtain satisfactory necrosis (at 400° C.). The operator then determines the volume of each injection and deduces from this the number of pulses needed to deliver the total volume of liquid. The triggering, travel, force and speed of the actuator are then programmed to inject N times the volume of liquid at regular intervals, in practice between 0.5 and 1 second per pulse duration of between 0.1 and 0.2 second. In an advantageous embodiment, the last pulse is of a duration greater than that of the preceding pulses for a same injected volume, this in order to heat the diffusion means before its withdrawal, thus avoiding the risk of proliferation of cancer cells into the healthy tissues.

The operation then starts by injecting the first volume of cold water into the heating unit. This volume is rapidly heated to 400° C., at a pressure of 250 bar (1 second per 1 ml with 2000 watts for water). Upon the following pulse of cold water, the heated water is propelled to the diffusion means after the valve (7) opens. The pressurized water exits the end of the tube or needle in the vapor state, then, as the temperature diminishes through release of heat into the tumor, the vapor transforms to hot water near to the boiling temperature, that is to say 100° C., the water then continuing to release heat. The injection of small volumes of water in the area of the apertures of the diffusion means results in a high localized output of heat, which is then diffused by thermal conduction.

In an advantageous embodiment, a small volume of cold water (2 to 5% of the volume of hot water) is sent into the conveying means and the diffusion means between each injection of pressurized hot water, this being done by programming of the solenoid valve (9). This variant avoids heating of the diffusion means, in particular the part not in contact with the healthy tissues between each injection.

The invention and the advantages which derive from it will be clear from the above description.

It will be noted in particular that the installation is able to ensure administration of heat directly within a body in a pulsed operation, thereby making it possible to treat cancer cells, and in particular tumors, by heat, and to do so with very small volumes of heated liquid. In addition, the use of the small volume of water avoids diffusion of heat outside the tumoral tissues and, moreover, the pulsed operation has the advantage of not causing uncontrolled heating of the diffusion means, and consequently necrosis of healthy tissues.

The invention claimed is:

1. An installation for delivering heat to all or part of human or animal cell tissue by means of a liquid, said installation comprising:
   a heating unit for heating said liquid,
   an injection unit for injecting liquid into the heating unit,
   a means for diffusion of the heated liquid,
   a means for conveying the heated liquid from the heating unit to the diffusion means,
   means for delivering the heated liquid at the diffusion means in a pulsed operation;
   wherein the heating unit is separated from the conveying means by a valve calibrated to a pressure at least equal to a saturation vapor pressure of the liquid to be injected.

2. The installation as claimed in claim 1, wherein the heating unit is in the form of a metal coil incorporating an electrical resistor or a heat exchanger around which there is wound a stainless steel tube whose internal diameter is between 0.1 and 0.5 mm, a length of the tube varying between 1500 and 5000 mm.

3. The installation as claimed in claim 1, further comprising a cold water branch circuit having a point of departure positioned between the injection unit and the heating unit, and a point of arrival positioned downstream of the valve, said branch circuit being connected at the point of departure by means of a programmable high-pressure solenoid valve.

4. The installation as claimed in claim 1, wherein the conveying means is in the form of a hollow tube with an internal diameter of between 50 and 150 µm, and a length of the tube being between 40 and 80 cm.

5. The installation as claimed in claim 1, wherein the diffusion means is in the form of a hollow tube whose distal end is closed off and whose walls are provided in whole or in part with substantially circular apertures having a diameter of between 30 and 70 µm, an external diameter of the tube being between 100 and 250 µm, while an internal diameter is between 50 and 150 µm.

6. The installation as claimed in claim 1, wherein the diffusion means is in the form of a rigid needle whose distal end is closed off and whose walls have, along all or part of their length, apertures with a diameter of between 30 and 70 µm, an internal diameter of the needle being between 0.05 and 0.2 mm, while an external diameter is between 0.2 mm and 0.7 mm, length being between 100 and 200 mm.

7. The installation of claim 6, wherein said substantially circular apertures have a diameter of 50 µm.

8. An installation for delivering heat to all or part of human or animal cell tissue by means of a liquid, said installation comprising:
   a heating unit for heating said liquid,
   an injection unit for injecting said liquid into the heating unit,
   a means for diffusion of heated liquid,
   a means for conveying the heated liquid from the heating unit to the diffusion means,
   means for delivering the heated liquid at the diffusion means in a pulsed operation;
   wherein the injection unit injects the liquid into the heating unit at a pressure greater by at least 50 bar, advantageously 100 bar, than the saturation vapor pressure of said liquid to be injected; and
   wherein the heating unit is separated from the conveying means by a valve calibrated to a pressure at least equal to a saturation vapor pressure of the liquid to be injected.

* * * * *